United States Patent [19]

Allport

[11] 4,047,029

[45] Sept. 6, 1977

[54] SELF-COMPENSATING X-RAY OR γ-RAY THICKNESS GAUGE

[76] Inventor: John J. Allport, 12298 Candy Court, Saratoga, Calif. 95070

[21] Appl. No.: 702,285

[22] Filed: July 2, 1976

[51] Int. Cl.² .................... G01N 23/20; G01N 23/00
[52] U.S. Cl. .............................. 250/273; 250/358 R
[58] Field of Search ............... 250/272, 273, 274, 277, 250/278, 279, 358 R, 359, 360, 308

[56] References Cited
U.S. PATENT DOCUMENTS 3,210,545  10/1965  Barnett .................. 250/358 R X
3,569,708  3/1971   Weinbaum et al. .......... 250/360

Primary Examiner—Davis L. Willis
Attorney, Agent, or Firm—Thomas Schneck, Jr.

[57] ABSTRACT

A gauge for determining the mass per unit area, or alternatively the thickness of sheet material by measuring the attenuation, as well as backscatter, of an X-ray beam or the like, while continuously taking into account deviations and changes in localized material composition, insofar as these have an effect on the transmission coefficient of the beam. Electrical signals representing these deviations are combined with calibration data for given material nominal properties, i.e., nominal composition. The resultant and output signal represents the mass per unit area or thickness.

16 Claims, 1 Drawing Figure

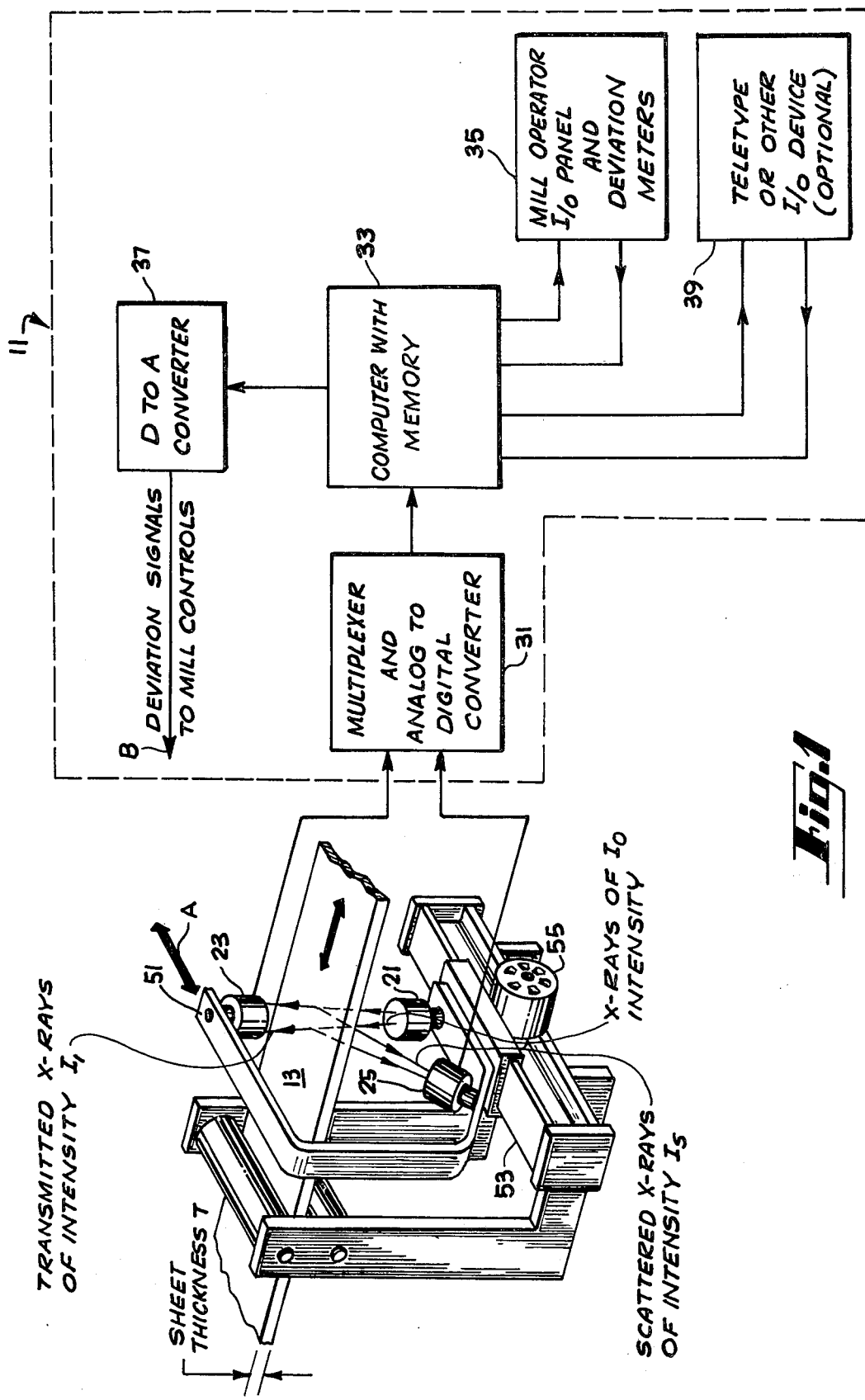

SELF-COMPENSATING X-RAY OR γ-RAY THICKNESS GAUGE

BACKGROUND OF THE INVENTION a. Field of the Invention

The invention relates generally to the measurement of instantaneous mass per unit area or thickness of sheet material as it passes a gauging station. More particularly the invention relates to apparatus for measuring mass per unit area or thickness of sheet material taking into account the effect of changes in composition from nominal values as such changes effect the material's transmission coefficient for X-rays and the like.

b. Prior Art

In manufacturing such as the rolling of steel, stainless steel, aluminum, copper and brass sheets, and the manufacturing of plastic sheets and the manufacture of paper, it is important to accurately measure the thickness of the material or the mass per unit area as the sheet material is manufactured. If the product is thicker or more massive than desired, the manufacturing material cost is increased. On the other hand, if the material is thinner or less massive than desired the material may be unsuitable for delivery and must be reworked in order to meet delivery specifications or scrapped.

Non-contact X-Ray gauging has been employed on a number of these processes for a number of years, and has been found to be the most satisfactory measurement technique. Other techniques such as contacting mechanical thickness measurement systems, and non-contacting beta-ray gauges have had only limited acceptance for a variety of reasons. Mechanical thickness measurements are undesirable because they may mark the material and because the delicate contacting member tends to "skip" and bounce on high speed sheets and give erroneous readings because of bounce from regions of varying thickness. In addition, mechanical gauges are easily destroyed when the sheet breaks and there is a crash or cobble in a metal rolling mill.

Radioisotope gauges have been employed with moderate success on these processes. However, because of the relatively low intensity of the radiation available, these gauges are not capable of providing a measurement in a short period of time which is sufficiently accurate for control of the machine. Typically, beta gauges require a signal averaging time of 5 seconds or more to achieve measurement accuracies of $\pm$ 0.5% to $\pm$ 0.25%. Modern metal rolling mills can be controlled in times of about 0.1 second or less and hence require thickness gauging with an accuracy of $\pm$ 0.25% or better in times of 0.01 second or less for optimum mill control. Radioisotope gauges have therefore only been useful in where slow speed control of the process is satisfactory, such as paper manufacture.

X-Ray gauges, on the other hand, permit high speed non-contact measurement with wide separation between the product and the measuring equipment. Because of the high intensity available from modern X-Ray equipment, signal averaging times of 0.01 to 0.005 seconds are generally all that is required to provide an accuracy of $\pm$ 0.25% in the measurement. Nevertheless, because the thickness or mass per unit area is deduced from the absorption of the X-Rays passing through the material and since the X-Ray technique is very sensitive to the composition of the material, large errors in the measurement can and do result from rather minor variations in composition.

For a typical X-Ray gauge the ratio ($R_1$) of the intensity of the radiation transmitted through the sheet ($I_1$) to that detected in the absence of the sheet ($I_0$) may be written:

$$R_1 = \frac{I_1}{I_0} = e^{-\mu_1 m} = e^{-\mu_1 \rho T}$$

where $m$ is the mass per unit area of the sheet material, and $\mu_1$ is the apparent mass absorption coefficient, $\rho$ is the density, and $T$ is the thickness. Although the absorption of the radiation is due to the mass per unit area of the material in the sheet, each alloy has a known density, which does not vary significantly with minor changes in composition, hence the transmission of radiation may be related directly to thickness. The apparent absorption coefficient results from photoelectric absorption of the X-Rays in the material, and from the coherent and incoherent (Compton) scattering of some of the X-Ray photons out of the angle of acceptance of the detector. Photoelectric absorption is however the predominant effect in these X-Ray thickness gauges. It is clear from equation 1 that precise determination of the true material thickness is reliant upon the absorption coefficient $\mu_1$ remaining constant and equal to the absorption coefficient determined for the gauge and the particular material composition at the time the gauge is calibrated.

For example many aluminum alloys contain zinc and/or copper concentrations of as much as 5% to 7% with allowable tolerances of about $\pm$ 0.5% in these elements for a given alloy. If, however, the composition of an aluminum alloy containing zinc shifts slightly say from 4.5% zinc at calibration to 5% zinc in the actual material, a shift in the zinc concentration of 0.5%, the percent error in the thickness measurement may be shown to be about 5% since the absorption coefficient of zinc is approximately 10 to 11 times that of aluminum in the X-Ray energy range of interest (20 to 25 KV). Similar types of errors may occur in steel rolling processes where the concentration of elements such as molybedenum may vary slightly, in copper and brass rolling where the concentration of zinc or lead may vary; and the plastic sheet manufacturing process the concentration of filler materials may vary. In the manufacture of paper substances containing elements such as silicon, calcium, and titanium, which are stronger X-ray absorbers, may be added to the basic paper fiber material to enhance the opacity.

The composition sensitivity of X-Ray thickness gauges outlined above has long been recognized as a primary problem in their use as a measurement tool. Certain U.S. patents teach apparatus for detecting composition variations, as well as use of backscatter radiation for gauging sheet thickness.

U.S. Pat. No. 2,966,587 shows a combination of radiation backscatter and attenuation detectors to determine the percent hydrogen and the hydrogen to carbon ratio of an hydrocarbon.

U.S. Pat. No. 3,188,471 reveals a coin identification apparatus that employs backscatter of beta radiation to determine the atomic number of the coin material, and the X-ray attenuation to determine the weight per unit area.

U.S. Pat. No. 3,499,152 shows a method and apparatus for improving radiation backscatter gauge response that employs a correction signal derived from an attenuation thickness measuring gauge. The fluorescence backscatter gauge is used to measure coating thickness and the attenuation gauge is used to derive a correction signal for variations of in the base thickness.

U.S. Pat. No. 3,569,708 shows a combination backscatter and attenuation gauge inspection apparatus that combines X-ray attenuation and backscatter signals to provide a more accurate indication of the wall thickness of a pipe.

It is an object of the present invention to devise a gauge for measuring weight per unit area of moving sheet material as it passes a gauging station taking into account localized changes in thickness and material composition by means of measuring backscatter and attenuation of an X-ray beam.

SUMMARY OF THE INVENTION

The above object is achieved with a system that generates an X-ray or gamma ray source mounted in gauging station with the beam directed perpendicularly through a sheet whose localized mass per unit area or instantaneous thickness if to be measured as the sheet moves past the gauging station. A pair of radiation detectors are positioned in the gauging station, one on the side of the sheet oposite the beam source to measure beam attenuation and another on the same side of the source to measure backscatter from the sheet. Each detector generates electrical signals proportional to the detected X-rays. These signals are fed to a connected computer which computes the transmission and scattering ratios for the material. In addition, the computing means includes a reference means with memory which has input derived from the material nominal properties as well as inputs from stored calibration data and from an operator. The computer utilizes this data to generate an adjusted absorption coefficient signal which is combined with the transmission ratio signal for computing mass per unit area and thickness.

The invention will be more clearly understood with reference to the figure.

BRIEF DESCRIPTION OF THE DRAWING

FIG. 1 is a plan view of the apparatus of the present invention.

DESCRIPTION OF THE PREFERRED EMBODIMENT

The present invention automatically corrects an X-Ray transmission gauge for shifts in material composition by not only detecting the X-radiation transmitted through the material, but also the X-radiation scattered from the material. The preferred embodiment is shown in FIG. 1 and employs a suitable source of X-radiation 21 and two detectors, detector 23 which detects the radiation transmitted through the material, and detector 25 which detects the radiation scattered from the material. The X-Ray source, 21, may in some instances where measurement speed is not a requirement, be replaced by a radioactive source of gamma rays or X-rays without change in the following description.

The X-radiation transmitted through the sheet, 13, is detected in the standard manner by detector 23, which may be, for example, in ionization chamber detector, a scintillation detector, or a solid state X-radiation detector. As noted earlier $$R_1 = e^{-\mu_1 \rho T} \qquad 2$$

where $\mu_1$ is the absorption coefficient of the material and $T$ is the thickness. The absorption coefficient $\mu_1$ is primarily influenced by the photoelectric effect, and is therefore quite sensitive to the material composition. A portion of the X-radiation scattered by the material is detected by a standard type detector 25 which may also for example be an ionization chamber detector, a scintillation detector, or a solid state X-radiation detector. By suitable filtering, detectors 23 and 25 are made nonresponsive to fluorescent X-Rays generated in the material by the action of the absorbed X-Rays generated at source 21.

The radiation detected by detector 25 is composed of X-Rays photons scattered from the material due to incoherent scattering (Compton effect or Compton scattering) and coherent scattering. Since coherent scattering takes place primarily in the forward direction, the radiation detected by detector 25 which is backscattered radiation is due primarily to the Compton effect. The intensity of the radiation scattered back to detector 25 from a volume element dv in a sheet of material is:

$$dI_s = HI_o e^{-2\mu_s \rho y} dy \qquad 3$$

where $H$ is a factor which is proportional to the scattering cross section of the material and the geometric location of detector 25 relative to source 21, and the acceptance angle for X-radiation of detector 25 and the cross sectional area of the X-ray beam, and $\mu_s$ is the apparent absorption coefficient for the scattered radiation. The letter $y$ designates an axis extending from source to detector 23, assuming the material whose thickness is to be measured has its thickness, T, parallel to the $y$ axis with $y=o$ designating the material edge closest to source 21 and $y=T$ designating the material edge closest to detector 23. The total scattered intensity ($I_3$) detected by detectro 25 is, by integration of equation 3, from $y = o$ to $y = T$ for constant $\rho$:

$$I_s = \frac{H}{2\mu_s \rho} I_0 (1 - e^{-2\mu_s \rho T}) \qquad 4$$

It can be seen from equation 4 that when the material becomes very thick, approaching infinite thickness, the detected scattered radiation approaches a constant value, $I_2$, where $$I_2 = \frac{H}{2\mu_s \rho} I_0 \qquad 5$$

If only source 21 and detector 25 are used to determine the thickness of a material where the absorption coefficient does not change with thickness and the composition does not change, the relation between thickness and $R_s$ is $$R_s = \frac{I_s}{I_2} = 1 - e^{-2\mu_s \rho T} \qquad 6$$

It should also be noted that in comparing two materials (1) and (2) of infinite thickness the ratio of the absorption coefficients at infinite thickness will be $$\left[ \frac{\mu_s(1)}{\mu_s(2)} \right]_\infty = \left[ \frac{I_s(2)}{I_s(1)} \right]_\infty = \left[ \frac{I_2(2)}{I_2(1)} \right] \qquad 7$$

In the present case the materials being measured are much less massive than the infinite mass discussed above. In transmission measurements using X-Ray absorption the optimum region for gauging is generally conceded to occur over the range $0.9 \geq R_1 \geq 0.1$, and hence the value of $R_s$ will nominally lie between approximately 0.20 and 0.99. The energy spectrum of the source 21 is chosen to place $R_1$ in the range noted above for the material of interest. For example, in the case of aluminum alloys of thicknes range 0.010 inch to 0.200 inch X-Rays of average energy approximately 22 KV are chosen.

The instrument is calibrated by measuring the transmission and scatter intensities and ratios from a series of known thicknesses and densities of mass per unit area samples of standard reference material having a constant composition such as pure aluminum. In addition, in the case of aluminum for example, the instrument is also calibrated by making the same measurements with a series of known thicknesses of each nominal alloy, where in the case of a particular nominal alloy the composition is uniform for all the thicknesses employed. The absorption coefficient for each nominal alloy, as well as the standard reference material, is then determined by using normal curve fitting techniques to fit the measured transmission ratios ($R_1$) to equation 2 and the measured scattering ratios ($R_s$) to equation 6 using the known thickness.

The X-Ray beam is usually composed of a range of energies and as the material becomes thicker more of the lower energy X-Rays are absorbed, causing the average energy of the transmitted beam to shift to a higher energy, which results in a variation of the absorption coefficient with thickness. The absorption coefficients determined from the calibration procedure are of the form:

$$\mu_1 = \mu_3 F(R_1) \quad \quad 9$$
and
$$\mu_s = \mu_4 G(R_1) \quad \quad 10$$

where $F(R_1)$ and $G(R_1)$ are polynomials in $R_1$, or functions of $R_1$, and $\mu_3$ and $\mu_4$ are the known values of $\mu_1$ and $\mu_1$ and $\mu_s$ at nearly infinite material thickness. The detected scattered radiation traverses, on average, a larger thickness of the material than the transmitted radiation and is therefore shifted somewhat more in energy than the transmitted beam, hence in general $\mu_1 \neq \mu_s$. The coefficients $\mu_3$ and $\mu_4$ are stored in a computer memory unit for each nominal alloy or composition.

For a thickness T of a given alloy the instrument measures the transmitted and scattered intensities and forms the ratios $R_1$ and $R_2$ where $R_1 = (I_1/I_o)$ and $R_2 = (I_s/I_{sr})$, where $I_{sr}$ is the value of the scattered intensity from very thick (mathematically of infinite thickness) standard reference material such a pure aluminum. The value of $I_{sr}$ has been determined during calibration of the instrument and is stored in the memory unit of computer 33. From equation 6 and 7

$$R_2 = \left[ \frac{\mu_{4r}}{\mu_4'} \right] \left[ 1 - e^{-2\mu_s \rho T} \right] \quad \quad 11$$

Defining A as:

$$A \equiv \frac{\mu_4 \, G(R_1)}{\mu_3 \, F(R_2)} = \frac{\mu_s}{\mu_1} \quad \quad 12$$

where $\mu'_4$ is the asymptotic value of the apparent absorption coefficient for the scattered radiation for the particular composition of the material in the gauge, and $\mu_{4r}$ is the asymptotic value of the apparent absorption coefficient for the scattered radiation from the very thick standard material, such as pure aluminum, as determined in a calibration procedure. And substituting $A\mu_1 = \mu_s$ into equation 11

$$R_2 = \left[ \frac{\mu_{4r}}{\mu_4'} \right] [1 - (R_1)^{2A}] \quad \quad 13$$

with the result $$\mu_4' = \mu_{4r} \left[ \frac{1 - (R_1)^{2A}}{R_2} \right] \quad \quad 14$$

At a particular transmission ratio $R_1$ the function $F(R_1)$ and $G(R_1)$ are constant, as is A, and $(\Delta\mu_1/\mu_1)$ the change in the absorption coefficient for transmitted radiation is then, from equation 12, equal to:

$$\frac{\Delta\mu_1}{\mu_1} = \frac{\Delta\mu_4}{\mu_4} = \frac{\mu_4' - \mu_4}{\mu_4} \quad \quad 15$$

The new corrected absorption coefficient $\mu_c$ for the transmitted radiation is then:

$$\mu_c = \mu_1 \left( 1 + \frac{\Delta\mu_4}{\mu_4} \right) \quad \quad 16$$

Using the new value $\mu_c$, the computer computes the composition corrected value of the thickness, $T_c$ as $$T_c = - \frac{1}{\rho \mu_c} \ln R_1 \quad \quad 17$$

thereby correcting for apparent errors in thickness due to shifts or differences from nominal alloy composition.

Operation of the apparatus of the present invention may be understood with reference to FIG. 1 in which analog signals from detectors 23 and 25, representing measured signal intensities $I_1$ and $I_s$ respectively, transmitted from the detectors 23 and 25 to the multiplexer and analog digital converter 31. A multiplexer is used to provide conventional time division or frequency division combination of the signals from detectors 23 and 25. The analog to digital converter is used to convert the multiplexed signal to the digital signal which can be processed by the computer 33.

Computer 33 is connected to the multiplexer and analog to digital converter 31 and includes a computer interface with that apparatus for conditioning the received signal to the proper format which is required by the computer 33. The computer 33 may be a general purpose computer while preferably a mini computer or micro processor which is adapted to carry out the mathematical equations described above, after such equations have been programmed into the computer 33. Electronic equipment 31, 33, 35, 37 and 39 may be mounted in a common housing 11 remote from source 21.

Basically, computer 33 forms the ratios $R_1$ and $R_2$ from the digitized intensities from detectors 23 and 25 and computes the correct material thickness in accord with equation 17 and the equations preceding it.

Previously it was stated that the instrument of the present invention is calibrated by measuring transmission and scattering intensities and ratios from a series of known thicknesses or mass per unit area of nominal materials having uniform compositions. From these calibration measurements corresponding nominal absorption coefficients are determined. Furthermore, the variation of absorption coefficient with increased sheet thickness was discussed with reference to equations 9 and 10 were in polynomial coefficients were derived to express the variation as a function of $R_1$. The calibration data, for each alloy or class of material including the standard or reference material is stored in the memory unit of computer 33 as $\mu_3$ and $\mu_4$ and the coefficients for the polynomials $F(R_1)$ and $G(R_1)$.

Since $\mu_1$ and $\mu_s$ are both functions of $R_1$, as well as the nominal alloy a teletype 39 or other input/output device 35 may be used to enter a specification of the nominal material into the computer for calling up a value for the polynomial coefficients and $\mu_3$ and $\mu_4$. Since $\mu_3$ and $\mu_4$ are the known values of $\mu_1$ and $\mu_s$ at nearly infinite material thickness and are also stored in the memory of computer 33, these values can be called up for a specified material to compute the coefficient A in accord with equation 11. It should be noted that $\mu'_4$ and $\mu_{4r}$ are respectively the asymptotic of value of the apparent absorption coefficient for a particular composition of a material and the aymptotic value of the apparent absorption coefficient for scattered radiation from very thick standard material, such as pure aluminum, respectively. These values enable a calculation of a corrected absorption coefficient $\mu_c$ in accord with equation 16. The corrected absorption coefficient $\mu_c$ is useful in calculating thickness in accord with equation 17 or mass per unit area in accord with the same equation by use of a simple density formula.

When the present apparatus is used for example in a rolling mill, a mill operator operates a panel 35 in which desired thicknesses and nominal alloy may be set and fed to computer 33. The thickness gauge then measures deviation from the target thickness and this value is expressed to a digital to analog converter 37 which provides an error or deviation signal to the rolling mill controls in the direction of the arrow B. The digital signal describing the deviation in measured thickness from target thickness as well as the target and actual thickness may be also supplied to other digital equipment used for controlling a rolling mill.

The following U.S. patents show how thickness signals are used in the prior art to control sheet thickness through a rolling mill: U.S. Pat. Nos. 3,843,434; 3,844,870; 3,930,922; 3,235,732.

The teletype 39 may be used either for communicating with computer 33 or obtaining typed data describing sheet thickness and deviation from the desired thickness.

In FIG. 1, the source 21 may be seen to be mounted on the metal frame 51 which also supports detectors 23 and 25. Frame 51 is mounted for motion on a rail 53 and may be moved across the path of travel of sheet 13 by means of a motor 55. In other words the source 21 may be made to scan across the width of sheet 13. The direction of motiom of the frame 51 is indicated by the arrow A above the detector 23.

While the computer 33 has been described as a general purpose computer or a mini computer or micro processor, it should be noted that such a computer may have all functional circuits needed to execute the equations described herein from the data specified. This may require a random access memory as well as programmable read only memory. Such memories and the circuits interconnecting the memories with the computer for assisting in the computations of the computer 33 are defined as reference means for receiving inputs from the operator panel 35 or the teletype 39 or both and for accessing stored calibration data, described above, inside of the reference means and interfacing with the arithmetic unit of the computer such that inputs representative of the transmission ratio $R_1$ and the scattering ratio $R_2$ may be combined as described above to produce the corrected absorption coefficient $\mu_c$. Such reference means also has circuits within defined as circuit means interacting with the computing means for receiving the corrected absorption coefficient $\mu_c$ and the transmission ratio signal $R_1$ to generate true mass per unit area signals as well as true thickness signals where the material density is known.

The operation of the apparatus may be described as follows:

a. Calibrate the instrument as described, determining $I_o$, $\mu_3$, $\mu_4$, coefficients for polynomials $F(R_1)$, $G(R_1)$; $I_{sr}$, $\mu_{4r}$, $\rho$, and store these quantities in the computer memory for each alloy or material.

b. Specify to the computer the alloy or material and the thickness thereof, thereby specifying in the computer particular $\mu_3$, $\mu_4$, as well as specific coefficients for the polynomials $F(R_1)$ and $G(R_1)$, $\rho$.

c. Measure $I_o$ again and revise $I_{sr}$ proportionally to $I_o$ if $I_o$ is different from the value determined in the calibration step. Also measure $I_1$ and $I_s$.

d. Compute $R_1$ and recall $I_{sr}$, then compute $R_2$.

e. Compute A by recalling $\mu_3$, $\mu_4$, $F(R_1)$, $G(R_1)$ after inserting $R_1$ in the polynomial equations.

f. Compute $\mu'_4$ using A in equation 14, as well as Rhd 1, $R_2$ and $\mu_{4r}$. Next compute $(\Delta\mu_4/\mu_4)$ using $\mu'_4$ and $\mu_4$. Then compute $\mu_1$ using $R_1$ and $\mu_3$ and $F(R_1)$. Then multiply $\mu_1$ by $$(1 + \frac{\Delta\mu_4}{\mu_4})$$

in accord with equation 16 to obtain $\mu_c$.

g. Compute T or $\rho$T in accord with equation 17. The above steps identify procedures for utilizing data gathered by the detectors of the present invention, as well as known data and specified quantites. The sequence of operations may be varied by those skilled in the art while remaining within the spirit and scope of the present invention.

I claim:

1. A system for continuously measuring the mass per unit area of sheet material, whose composition is slightly variable from nominal comprising, radiation generating means for generating a radiation beam directed into said sheet, said radiation having sheet in a straight line from said generating means and a second portion of said beam is scattered from said sheet, first detector means positioned on the opposite side of said sheet from said radiation generating means in a position to intercept said first portion of said beam for measuring the intensity of said first portion of said beam, and having a first output signal representative of beam intensity transmitted through said sheet material, second detector means disposed in a position to intercept part of said second beam portion for measuring the intensity of said part and having a second output signal representative of beam intensity scattered from said sheet material, computing means connected to said first and second detector means for continuously computing the transmission ratio, $R_1$, by dividing said first output signal by the signal output of said first detector means in the absence of sheet material and computing the scattering ratio, $R_2$, by dividing said second output signal by the signal output of said second detector means in the presence of very thick standard sheet material, said transmission and scattering ratios, $R_1$ and $R_2$ being represented by electrical signals, said computing means including reference means for receiving inputs of nominal material composition and for having stored calibration data therein with respect to said material composition and further having as inputs said signals representative of said transmission ratio, $R_1$, and said scattering ratio, $R_2$, said computing means using said ratios $R_1$ and $R_2$ with said calibration data and having as an output a corrected absorption coefficient signal $\mu_c$, said reference means having circuit means interacting with said computing means for receiving said absorption coefficient signal $\mu_c$ and said transmission ratio signal $R_1$ for generating a material mass per unit area signal, $\rho T$, and an output means for delivering said mass per unit area signal.

2. The system of claim 1 wherein said reference means being operatively connected in said computing means by circuit means for presenting as electrical signals absorption coefficients, $\mu_3$ and $\mu_4$, for transmitted and scattered radiation for very massive and thick materials, said connected computing means generating respective polynomials, $F(R_1)$ and $G(R_1)$, and associated electrical signals to be multiplied by respective absorption coefficients of very massive and thick materials, $\mu_3$ and $\mu_4$, respectively, for defining signals representing nominal absorption coefficients for radiation transmitted and scattered by the material under test.

3. The system of claim 2 wherein said polynomials are electrically specified in said random access memory by specification of a nominal material for said sheet material.

4. The system of claim 3 wherein said computing means generates a factor A, dependent on the transmission ratio $R_1$, by means of the equation $$A = \frac{\mu_4 G(R_1)}{\mu_3 F(R_1)}$$

and an electrical signal proportional thereto.

5. The system of claim 4 wherein said computing means has as inputs electrical signals representing A, $R_1$, $R_2$, and $\mu_{4r}$ where $R_1$ is the transmission ratio signal, $R_2$ is the scattering ratio signal, and $\mu_{4r}$ is an asymptotic value of the apparent absorption coefficient signal for scattered radiation from very massive and thick standard material, said computing means having circuit means for generating a signal representing the corrected absorption coefficient for scattered radiation, $\mu'_4$, for a very massive and thick sheet of material of the same composition as that being measured.

6. The system of claim 5 wherein said signal representing $\mu'_4$ is generated by electrical combination of signals for $A_1$, $R_1$, $R_2$ and $\mu_{4r}$ in accord with the equation $$\mu_4' = \mu_{4r} \frac{[1 - (R_1)^{2A}]}{R_2}$$

7. The system of claim 6 wherein said computing means has as inputs electrical signals representing $\mu'_4$, $\mu_4$, $\mu_3$, $F(R_1)$, said computing means having circuit means for generating a signal representing the corrected absorption coefficient $\mu_c$ for radiation transmitted through the material.

8. The system of claim 7 wherein said computing means has as inputs electrical signals representing the corrected absorption coefficient, $\mu_c$, and transmission ratio $R_1$, said computing means having circuit means for generating a signal representing mass per unit area of said sheet material.

9. The system of claim 8 wherein said computing means has as inputs electrical signals representing the mass per unit area of said sheet material and the known density of said sheet material, said computing means having circuit means for generating a signal representing thickness of said sheet material.

10. The apparatus of claim 1 wherein said radiation generating means is an X-ray source.

11. The apparatus of claim 1 wherein said radiation generating means is a gamma ray source.

12. A method for continuously measuring mass per unit area of sheet material whose composition is slightly variable in comparison to nominal material comprising, generating a beam of penetrating radiation, measuring the intensity of said beam of penetrating radiation, directing said beam of penetrating radiation into a sheet material, measuring the intensity of said radiation transmitted through said sheet material, measuring the intensity of said radiation scattered by said material, dividing said measured transmitted intensity by said measured beam intensity to form a beam transmission ratio, dividing said measured scattered intensity by the scattered intensity expected from a very massive and thick standard material to form a beam scattering ratio, comparing said beam scattering ratio with another scattering ratio expected from a nominal material at said transmission ratio, calculating for said sheet material a corrected material absoption coefficient for transmission of penetrating radiation using said scattering ratio comparison, and calculating the mass per unit area of said sheet material using said transmission ratio and said corrected absorption coefficient.

13. The method of claim 12 further defined by continuously dividing the calculated mass per unit area of said sheet material by the known density of said material thereby yielding the thickness of sheet material whose composition is slightly variable in comparison to material of nominal composition.

14. The method of claim 12 wherein said penetrating radiation is X-ray radiation.

15. The method of claim 12 wherein said penetrating radiation is Gamma radiation.

16. The method of claim 12 wherein said scattered radiation is backscattered from said sheet material.

* * * * *

UNITED STATES PATENT AND TRADEMARK OFFICE
CERTIFICATE OF CORRECTION

PATENT NO. : 4,047,029

DATED : September 6, 1977

INVENTOR(S) : John J. Allport

It is certified that error appears in the above-identified patent and that said Letters Patent are hereby corrected as shown below:

Claim 1 - Col. 8, lines 67 and 68
    insert after "radiation having"
    --energy such that a first portion of said beam penetrates
      said--

Claim 12 - Col. 10, line 61
    "absoption" should read
    --absorption--

UNITED STATES PATENT AND TRADEMARK OFFICE
CERTIFICATE OF CORRECTION

PATENT NO. : 4,047,029

DATED : September 6, 1977

INVENTOR(S) : John J. Allport

It is certified that error appears in the above-identified patent and that said Letters Patent are hereby corrected as shown below:

Col. 1, line 16
"In manufacturing such" should read
--In manufacturing processes such--

Col. 3, line 22
"thickness if to be measured" should read
--thickness is to be measured--

Col. 4, line 36
"intensity $(I_3)$" should read
--intensity $(I_s)$--

Col. 4, line 37
"detectro" should read
--detector--

Col. 5, line 44
delete "$\mu_1$ and"

Col. 8, lines 45 and 46
"Rhd 1" should read
--$R_1$--

Signed and Sealed this

Third Day of November 1981

[SEAL]

Attest:

Attesting Officer

GERALD J. MOSSINGHOFF

Commissioner of Patents and Trademarks